(12) United States Patent
Sanchez

(10) Patent No.: US 8,599,027 B2
(45) Date of Patent: Dec. 3, 2013

(54) APPARATUS AND METHOD FOR ALERTING MACHINE OPERATOR RESPONSIVE TO THE GAZE ZONE

(75) Inventor: Julian Sanchez, Shoreview, MN (US)

(73) Assignee: Deere & Company, Moline, IL (US)

( * ) Notice: Subject to any disclaimer, the term of this patent is extended or adjusted under 35 U.S.C. 154(b) by 538 days.

(21) Appl. No.: 12/907,628

(22) Filed: Oct. 19, 2010

(65) Prior Publication Data
US 2012/0092173 A1  Apr. 19, 2012

(51) Int. Cl.
*G08B 23/00* (2006.01)
*B60Q 1/00* (2006.01)
*G06G 7/78* (2006.01)

(52) U.S. Cl.
USPC .......... 340/576; 340/435; 340/436; 340/438; 340/439; 340/573.1; 701/300; 701/301

(58) Field of Classification Search
None
See application file for complete search history.

(56) References Cited

U.S. PATENT DOCUMENTS

| | | | | |
|---|---|---|---|---|
| 6,154,559 | A * | 11/2000 | Beardsley | 382/103 |
| 6,578,962 | B1 | 6/2003 | Amir et al. | |
| 6,972,733 | B2 | 12/2005 | Maguire, Jr. | |
| 7,605,694 | B2 | 10/2009 | Prost-Fin et al. | |
| 7,620,202 | B2 | 11/2009 | Fujimura et al. | |
| 8,085,140 | B2 * | 12/2011 | Mochizuki et al. | 340/438 |
| 8,144,002 | B2 * | 3/2012 | Kiuchi | 340/435 |
| 8,269,652 | B2 * | 9/2012 | Seder et al. | 340/903 |
| 8,384,531 | B2 * | 2/2013 | Szczerba et al. | 340/435 |
| 2002/0011928 | A1 * | 1/2002 | Williams | 340/436 |
| 2004/0150514 | A1 * | 8/2004 | Newman et al. | 340/435 |
| 2007/0164990 | A1 | 7/2007 | Bjorklund et al. | |
| 2009/0167516 | A1 * | 7/2009 | Kogawara et al. | 340/439 |
| 2009/0243880 | A1 * | 10/2009 | Kiuchi | 340/903 |
| 2010/0253492 | A1 * | 10/2010 | Seder et al. | 340/435 |
| 2010/0253526 | A1 * | 10/2010 | Szczerba et al. | 340/576 |
| 2010/0289632 | A1 * | 11/2010 | Seder et al. | 340/436 |
| 2011/0169625 | A1 * | 7/2011 | James et al. | 340/439 |
| 2011/0199202 | A1 * | 8/2011 | De Mers et al. | 340/439 |

FOREIGN PATENT DOCUMENTS

| | | |
|---|---|---|
| EP | 1583035 A2 | 5/2005 |
| EP | 2061016 A1 | 5/2009 |
| WO | 2009060172 A1 | 5/2009 |

OTHER PUBLICATIONS

EP Search Report dated Feb. 10, 2012, 8 pages.
Sanchez et al., "Operator-Automation Interaction in Agricultural Vehicles", Ergonomics in Design, 2009, pp. 14-19.
Shepley et al., "Eye-Tracking Analysis of Near-Term Terminal Automation for Arrival Coordination", American Institute of Aeronautics and Astronautics, 2009 The Mitre Corporation, pp. 1-1.
Sanchez et al., "Controller-automation Interaction in NextGen: A New Paradigm", 2010, The Mitre Corporation, pp. 1-21.

* cited by examiner

*Primary Examiner* — Julie Lieu
(74) *Attorney, Agent, or Firm* — Yee & Associates, P.C.

(57) ABSTRACT

The different illustrative embodiments provide a method, apparatus, and computer program product for generating alerts. Responsive to an occurrence of an event, a current gaze zone in a plurality of gaze zones associated with a current view of an operator is identified. A desired gaze zone in the plurality of gaze zones is identified for the event. The desired gaze zone contains a source location for the event. A determination is made whether the current gaze zone is inside the desired gaze zone. Responsive to a determination that the current gaze zone is outside the desired gaze zone, an alert is generated.

25 Claims, 9 Drawing Sheets

APPARATUS AND METHOD FOR ALERTING MACHINE OPERATOR RESPONSIVE TO THE GAZE ZONE

FIELD OF THE INVENTION

The present invention relates generally to detecting head and eye movement of an operator, and more specifically to the generation of alerts.

BACKGROUND OF THE INVENTION

A machine operator focuses on events occurring in and around the machine to safely and correctly operate the machine. However, the machine operator may become distracted and lose focus on the events and/or the operation of the machine. In some situations, the operation of the machine is complex such that the safe operation of the machine involves directing the focus of the operator on numerous different areas without knowing which one of the many areas now requires, at any given instance in time based upon operating environment events, his or her immediate attention.

Alerts are commonly generated for operators of machines when a condition is present that requires the attention of the operator. For example, when the machine is a computer, some of the alerts generated may include a popup and/or sound to alert the user of an upcoming calendar event. Such an alert is advantageous for the computer operator because the computer operator may not be focused on the calendar. Other known alerts include beeping sounds when a motor vehicle backs up to alert nearby pedestrians who may not be paying attention to this specific vehicle; or other beeping tones when a seatbelt has not yet been fastened to alert the occupant of a motor vehicle.

SUMMARY

The different illustrative embodiments provide a method, apparatus, and computer program product for generating alerts. Responsive to an occurrence of an event, a current gaze zone in a plurality of gaze zones associated with a current view of an operator is identified. A desired gaze zone in the plurality of gaze zones is identified for the event. The desired gaze zone contains a source location for the event. A determination is made whether the current gaze zone is inside the desired gaze zone. Responsive to a determination that the current gaze zone is outside the desired gaze zone, an alert is generated.

The features, functions, and advantages can be achieved independently in various embodiments of the present invention or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and advantages thereof, will best be understood by reference to the following detailed description of an illustrative embodiment of the present invention when read in conjunction with the accompanying drawings, wherein:

DETAILED DESCRIPTION

Figure 1:
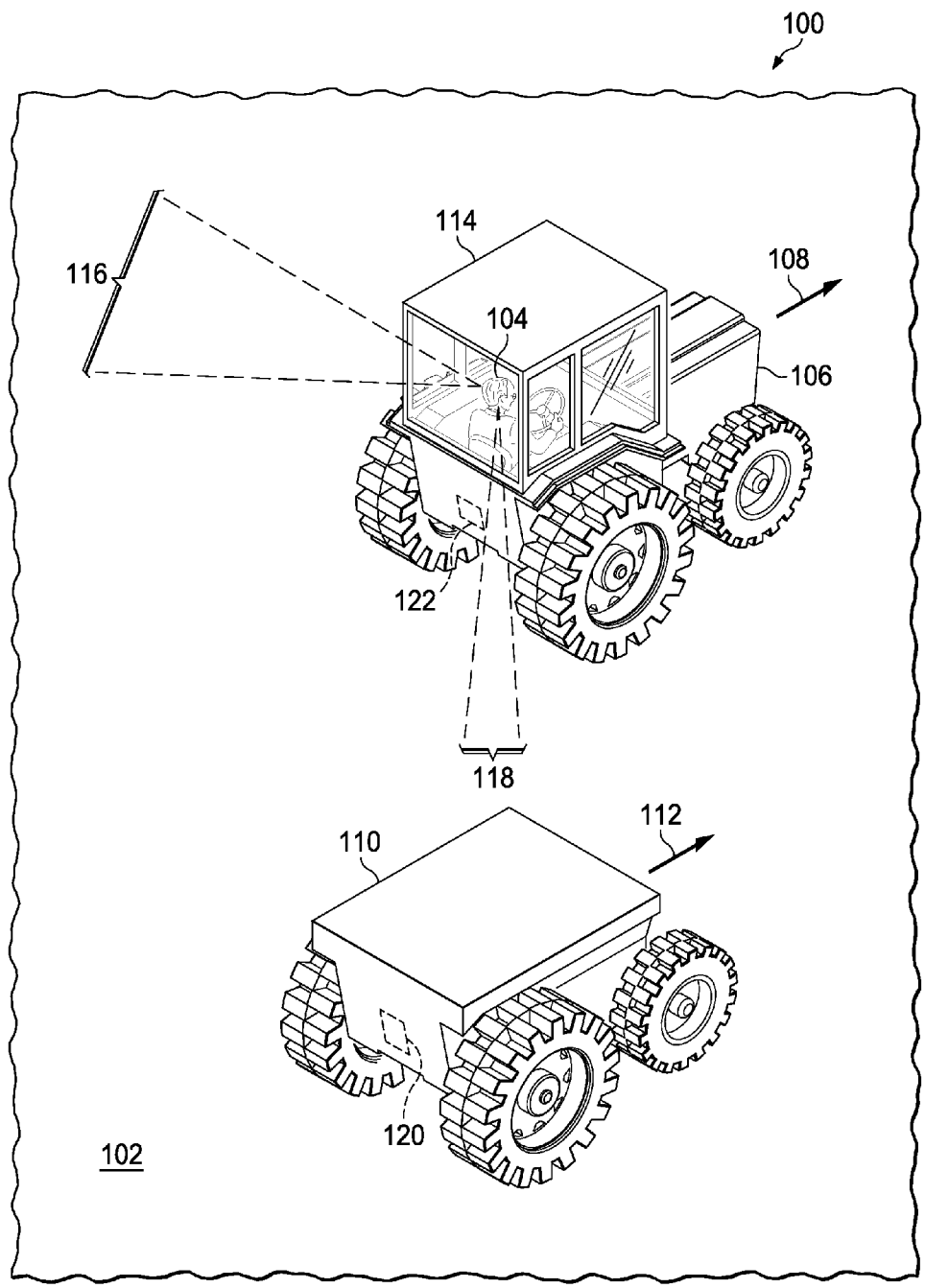
FIG. 1 is an illustration of an alert generation environment depicted in accordance with an illustrative embodiment.

With specificity to the figures, and more specifically FIG. 1, an illustration of an alert generation environment is depicted in accordance with an illustrative embodiment. Alert generation environment 100 is an example of an environment in which illustrative embodiments may be implemented.

In this illustrative example, alert generation environment 100 contains area 102. Area 102 is a field in these examples. Area 102 may be an area of a field in which agricultural crops are grown. Operator 104 operates vehicle 106 in area 102. In these examples, operator 104 drives vehicle 106 through area 102 in direction 108. Vehicle 106 is a tractor in these examples. However, vehicle 106 may be any mobile platform operated by operator 104. For example, vehicle 106 may be an automobile, a mower, a harvester, a sprayer, or another suitable vehicle.

Vehicle 110 also operates in area 102. Vehicle 110 is a follower vehicle in these examples. A follower vehicle is a vehicle that travels along a path and/or in a direction traveled by a leader vehicle. In these examples, vehicle 106 is the leader vehicle for vehicle 110. Thus, vehicle 110 travels in direction 112 to follow vehicle 106 traveling in direction 108.

Operator 104 is located in cab 114 of vehicle 106. Cab 114 is an area of vehicle 106 where navigational controls for vehicle 106 are located. Of course, operator 104 may be located outside of vehicle 106 in other illustrative embodiments. A gaze zone monitoring system onboard vehicle 106 identifies the direction in which operator 104 is looking by identifying the gaze zone of cab 114 through which operator 104 is looking. A gaze zone is a region of cab 114. The gaze zone is used to identify a location or direction in which operator 104 is presently focused. The gaze zone is also used to identify a direction which operator 104 should be focused in order to properly operate vehicle 106 and/or vehicle 110. In this illustrative embodiment, operator 104 is looking in direction 116.

When an event occurs, the gaze zone monitoring system onboard vehicle 106 also identifies a desired gaze zone for operator 104. The event is an occurrence for which the focus of the operator is used in a particular location to continue proper operation of vehicle 106 and/or vehicle 110. For example, the event may be an inconsistency developing on vehicle 110. In one illustrative example, a combine associated with vehicle 110 becomes blocked such that the combine may not continue operation. The desired gaze zone is the gaze zone which operator 104 uses to focus on the location of the event. In this illustrative example, the desired gaze zone is desired gaze zone 118.

Desired gaze zone 118 may be identified from the gaze zones available in cab 114 by identifying a location of the source location for the event. In this illustrative embodiment, vehicle 110 is the source location for the event. In such illustrative embodiments, sensors onboard vehicle 110 identify the occurrence of the event.

Vehicle 110 uses location monitoring system 120 to identify the location of vehicle 106. Vehicle 110 may use an onboard communication system, such as a radio transmitter, to send the location of vehicle 110 to vehicle 106 and an indication that the event has occurred. Of course, in other illustrative embodiments, the source location may be a particular portion of vehicle 110. For example, the source location for the event may be a combine pulled by vehicle 110.

Vehicle 106 may contain a controller that receives the location of vehicle 110. The controller may also receive the location of vehicle 106 from location monitoring system 122 onboard vehicle 106. In some illustrative embodiments, location monitoring systems 120 and 122 are global positioning system receivers. However, in other illustrative embodiments, location monitoring systems 120 and 122 are relative positioning systems. For example, location monitoring system 120 may be a radio frequency identifier tag and location monitoring system 122 may be one or more radio frequency identifier receivers.

Once the controller onboard vehicle 110 identifies the location of vehicle 110 relative to vehicle 106, the gaze monitoring system translates the relative location to a desired gaze zone in cab 114. The controller onboard vehicle 106 then determines whether gaze zone 116 is within the desired gaze zone. In this example, gaze zone 116 is not within desired gaze zone 118.

Thus, the controller notifies an alert system onboard vehicle 106 to generate an alert. The alert may be audio, visual, vibratory, or any combination thereof. The alert system generates the alert. The alert may be presented on a screen, a control panel, using one or more lights, using a speaker, or another suitable alert system. In some illustrative embodiments, the alert is generated within desired gaze zone 118. Generating the alert within desired gaze zone 118 means that the alert system generating the alert is located at least partially in desired gaze zone 118 in cab 114. For example, the alert may be an audio alert generated using a speaker located within desired gaze zone 118 in cab 114. On the other hand, in the event that the gaze zone of the operator is within the desired gaze zone, no alert is generated.

The illustration of alert generation environment 100 is not meant to imply physical or architectural limitations to the manner in which different advantageous embodiments may be implemented. For example, vehicle 106 and/or vehicle 110 may be autonomous vehicles in some illustrative embodiments.

For example, vehicle 106 and/or vehicle 110 may follow a predetermined path through area 102. Alternatively, vehicle 106 and/or vehicle 110 may be configured to perform an operation in area 102. The path of vehicle 106 and/or vehicle 110 may be determined by using sensors for the operation being performed. For example, in illustrative embodiments in which vehicle 106 and vehicle 110 perform a mowing operation in area 102, vehicle 106 and/or vehicle 110 may use sensor systems to identify portions of area 102 with vegetation greater than a particular length. Vehicles 106 and/or 110 may then generate a path to perform the mowing operation in such a portion of area 102.

The different illustrative embodiments recognize and take into account a number of different considerations. For example, the different illustrative embodiments recognize that an operator of a machine, such as a vehicle, may be focusing on an object or area other than the object or area used in proper operation of the vehicle or machine. Proper operation is operation of the machine in accordance with recommendations of the manufacturer of the machine. For example, the operator may be focusing on conversation with another person instead of the operation of a blade on a wood chipper.

The different illustrative embodiments also recognize that the area of focus of an operator may be identified by identifying the gaze direction of the operator. Gaze direction is the direction in which the operator is looking. For example, when an operator is focusing on a conversation with another person instead of the operation of a blade on a wood chipper, the different illustrative embodiments recognize that the operator is likely looking at the other person and not the blade on the wood chipper.

The different illustrative embodiments also recognize and take into account that an operator may focus on an object or area used in proper operation of a vehicle or machine when alerted to do so. For example, a voice alert audible to the operator indicating that an inconsistency is developing in the blade of the wood chipper may cause the operator to change the focus of the operator to the blade of the wood chipper. However, generating alerts when the operator is already focused on the object or area used in proper operation of the vehicle or machine is disadvantageous because the alert may bother the operator and cause the operator to be less sensitive to future alerts.

Thus, the different illustrative embodiments provide a method, apparatus, and computer program product for generating alerts. Responsive to an occurrence of an event, a current gaze zone in a plurality of gaze zones associated with a current view of an operator is identified. A desired gaze zone in the plurality of gaze zones is identified for the event. The desired gaze zone contains a source location for the event. A determination is made whether the current gaze zone is inside the desired gaze zone. Responsive to a determination that the current gaze zone is outside the desired gaze zone, an alert is generated.

Figure 2:
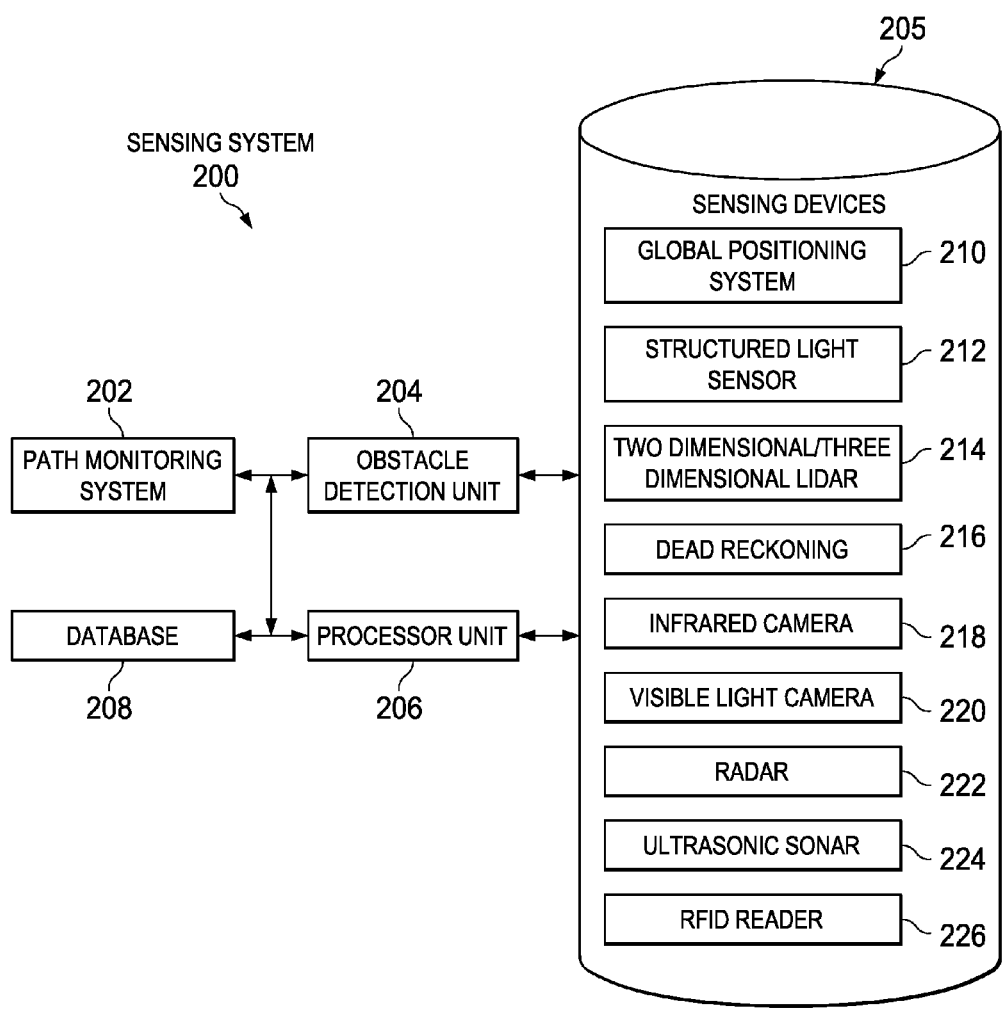
FIG. 2 is an illustration of a sensing system depicted in accordance with an illustrative embodiment.

Looking now to FIG. 2, an illustration of a sensing system is depicted in accordance with an illustrative embodiment. Sensing system 200 may be an example of a sensing system onboard vehicle 110 in FIG. 1. Sensing system 200 includes path monitoring system 202, obstacle detection unit 204, sensing devices 205, processor unit 206, and database 208.

In this illustrative embodiment, sensing system 200 may be onboard a follower vehicle, such as vehicle 110 in FIG. 1. However, sensing system 200 may also be located onboard an autonomous vehicle. An autonomous vehicle is a vehicle that initiates and performs an operation without needing interaction by a user. The operation may include moving the autonomous vehicle. The autonomous vehicle may move on a path generated by sensing system 200.

Path monitoring system 202 is used to monitor a path for the vehicle. In illustrative embodiments in which the vehicle is a follower vehicle, path monitoring system 202 monitors a path on which a leader vehicle moves, such as vehicle 106 in FIG. 1. Path monitoring system 202 acquires data regarding vehicle and/or leader vehicle direction and vehicle speed of the vehicle and/or leader vehicle. Path monitoring system 202 may acquire a sequence of positions from, for example, global positioning system 210. This acquired data may be sent to a data processing system for processing and/or storage, such as data processing system 300 in FIG. 3. For example, this data may be monitored continuously or periodically. Further, this data may be acquired as part of a predetermined navigational plan and stored in database 208.

In this illustrative example, sensing devices 205 are components of path monitoring system 202. As illustrated, sensing system 200 includes sensing devices 205 which may include, for example, global positioning system 210, structured light sensor 212, two dimensional/three dimensional light detection and ranging system 214, dead reckoning 216, infrared camera 218, visible light camera 220, radar 222, ultrasonic sonar 224, and radio frequency identification reader 226. These different sensors may be used to identify the area around a vehicle and/or the location of a leader vehicle relative to the vehicle. Sensing devices 205 in sensing system 200 may be selected such that one of the sensors is always capable of sensing information used to operate the vehicle in different operating environments.

Global positioning system 210 may identify the location of the vehicle with respect to other objects and/or obstacles in the environment. Global positioning system 210 may be any type of radio frequency triangulation scheme based on signal strength and/or time of flight. Structured light sensor 212 emits light in a pattern, such as one or more lines, reads the reflections of light through a camera, and interprets the reflections to detect and measure obstacles in the environment. Two dimensional/three dimensional light detection and ranging system 214 is an optical remote sensing technology that measures properties of scattered light to find range and/or other information of a distant target. Two dimensional/three dimensional light detection and ranging system 214 emits laser pulses as a beam, and then scans the beam to generate two dimensional or three dimensional range matrices. The range matrices are used to determine distance to an obstacle or surface by measuring the time delay between transmission of a pulse and detection of the reflected signal.

Dead reckoning 216 begins with a known position. Dead reckoning 216 is then advanced based upon known speed, elapsed time, and course. The advancement may be mathematically or directly. The advancement based upon speed may use the vehicle odometer, or ground speed radar, to determine distance traveled from the known position.

Infrared camera 218 detects heat indicative of a living thing versus an inanimate object. An infrared camera may also form an image using infrared radiation. Visible light camera 220 may be a standard still-image camera, which may be used alone for color information or with a second camera to generate stereoscopic or three-dimensional images. When visible light camera 220 is used along with a second camera to generate stereoscopic images, the two or more cameras may be set with different exposure settings to provide improved performance over a range of lighting conditions. Visible light camera 220 may also be a video camera that captures and records moving images.

Radar 222 uses electromagnetic waves to identify the range, altitude, direction, or speed of both moving and fixed obstacles. Radar 222 may be used in a time of flight mode to calculate distance to an obstacle, boundary, or other object. Radar 222 may also be used in Doppler mode to calculate the speed of a moving obstacle or object. Ultrasonic sonar 224 uses sound propagation on an ultrasonic frequency to measure the distance to an obstacle by measuring the time from transmission of a pulse to reception and converting the measurement into a range using the known speed of sound. Ultrasonic sonar 224 is well known in the art and can also be used in a time of flight mode or Doppler mode, similar to radar 222. Radio frequency identification reader 226 relies on stored data and remotely retrieves the data using devices called radio frequency identification (RFID) tags or transponders.

Sensing system 200 may retrieve data from one or more of sensing devices 205 to obtain different perspectives of the area in which the vehicle is operating. For example, sensing system 200 may obtain imaging data from visible light camera 220. Sensing system 200 may also obtain data about the distance of the vehicle in relation to obstacles in the environment from two dimensional/three dimensional light detection and ranging system 214. Sensing system 200 may also obtain location data of the vehicle in relation to a map from global positioning system 210.

In these illustrative examples, obstacle detection unit 204 is used to detect obstacles that may obstruct the vehicle, such as a rock or inconsistency in the ground in the area. Obstacle detection unit 204 uses data acquired from sensing devices 205 and/or path monitoring system 202 to identify areas where obstacles may affect operations of the vehicle. Obstacle detection unit 204 may detect obstacles by sending out and receiving a plurality of signals.

In this illustrative example, obstacle detection unit 204 may incorporate any number of sensing devices 205 to detect obstacles. For example, without limitation, obstacle detection unit 204 may incorporate ultrasonic sonar 224 or infrared camera 218 imaging to detect a density or temperature difference between grass to be mown and an obstacle that may present issues. In another example, obstacle detection unit 204 may incorporate ultrasonic sonar 224 to detect movement differences between grass that is relatively stationary and an obstacle such as an animal that may move.

In a further example, obstacles may be known and planned into a predetermined path. Path data may be stored in database 208. For example, obstacles may be located and identified by a human, by software analyzing an aerial image, by software analyzing images taken at or near ground level, and/or by sensing system 200.

Obstacle detection unit 204 is further configured to detect data regarding the size of the obstacle, the distance to the obstacle, and the position of the obstacle on the path. Obstacle detection unit 204 may incorporate data generated by any number of sensing devices 205, and/or any other suitable methods to detect the data about the obstacle.

Sensing system 200 is configured to send data from path monitoring system 202 and obstacle detection unit 204 to processor unit 206. Processor unit 206 may be an example of one implementation of processor unit 304 in FIG. 3. In this illustrative example, data received from obstacle detection unit 204 regarding the position of the obstacle on the path and the size of the obstacle may be used to determine a path that avoids contact with the obstacle.

However, the data received from obstacle detection unit 204 may also be used to identify that an event has occurred. For example, the event may be the vehicle encountering an obstacle causing the vehicle to change path or become unable to continue moving in the event that the obstacle has already been contacted. Of course, the event may be another type of event, such as an inconsistency developing in a tool being used by the vehicle.

The event and the location of the vehicle may be sent to another vehicle, such as vehicle 106 in FIG. 1, over a wireless link. The other vehicle may use the location and the event to generate an alert for an operator in the case that a determination is made that the gaze direction of the operator is not the same as a desired gaze direction. In this illustrative example, the desired gaze direction is the direction of the vehicle containing sensing system 200 relative to the other vehicle receiving the event and location of the vehicle.

Figure 3:
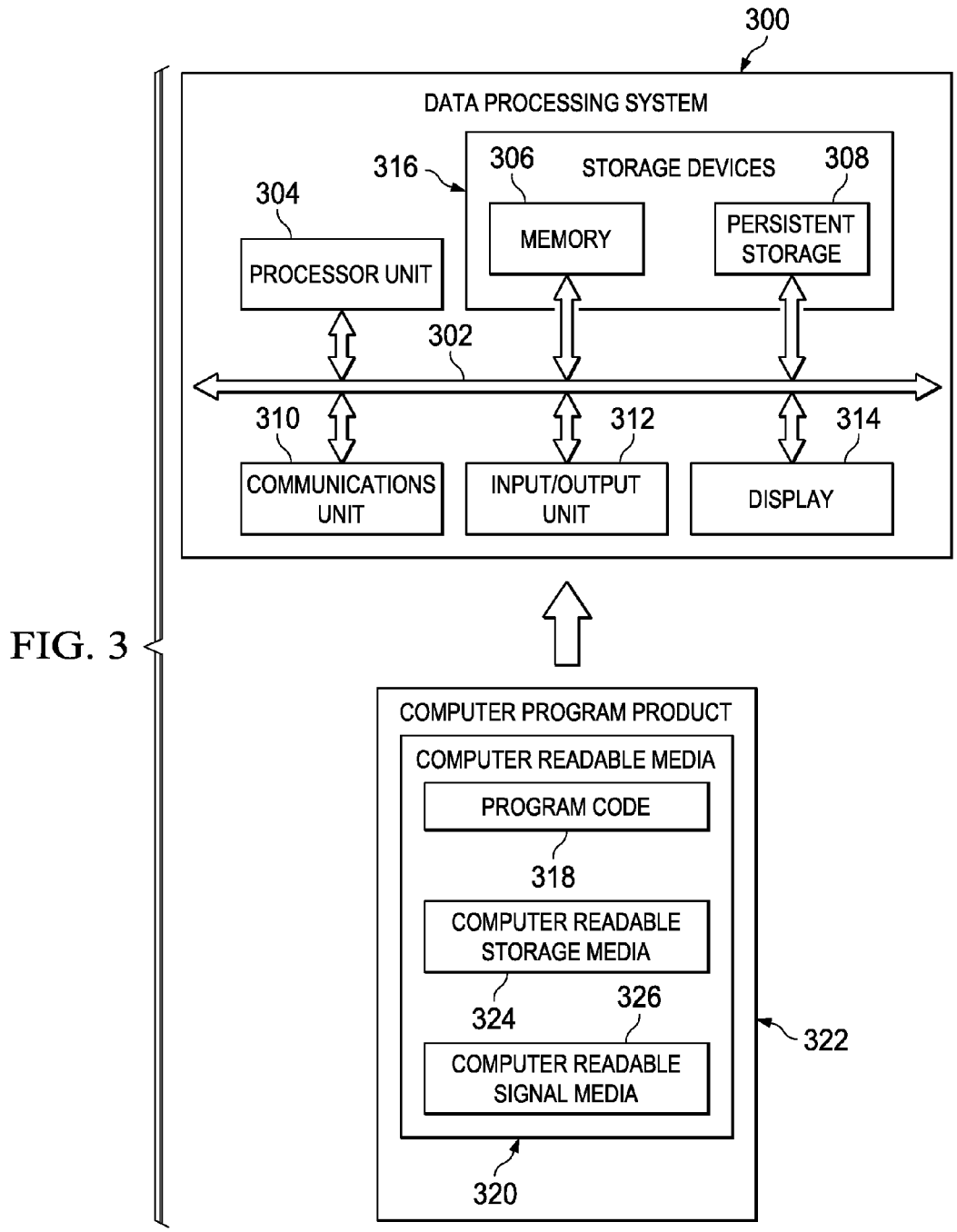
FIG. 3 is an illustration of a data processing system depicted in accordance with an illustrative embodiment.

Turning now to FIG. 3, an illustration of a data processing system is depicted in accordance with an illustrative embodiment. Data processing system 300 may be a controller onboard a vehicle, such as vehicle 106 in FIG. 1, or a component of the controller. Data processing system 300 may be used to determine whether a current gaze direction, such as gaze direction 116, is within gaze direction 118 in FIG. 1. In this illustrative example, data processing system 300 includes communications fabric 302, which provides communications between processor unit 304, memory 306, persistent storage 308, communications unit 310, input/output (I/O) unit 312, and display 314.

Processor unit 304 serves to execute instructions for software that may be loaded into memory 306. Processor unit 304 may be a number of processors, a multi-processor core, or some other type of processor, depending on the particular implementation. A number, as used herein with reference to an item, means one or more items. Further, processor unit 304 may be implemented using a number of heterogeneous processor systems in which a main processor is present with secondary processors on a single chip. As another illustrative example, processor unit 304 may be a symmetric multi-processor system containing multiple processors of the same type.

Memory 306 and persistent storage 308 are examples of storage devices 316. A storage device is any piece of hardware that is capable of storing information, such as, for example, without limitation, data, program code in functional form, and/or other suitable information either on a temporary basis and/or a permanent basis. Storage devices 316 may also be referred to as computer readable storage devices in these examples. Memory 306, in these examples, may be, for example, a random access memory or any other suitable volatile or non-volatile storage device. Persistent storage 308 may take various forms, depending on the particular implementation.

For example, persistent storage 308 may contain one or more components or devices. For example, persistent storage 308 may be a hard drive, a flash memory, a rewritable optical disk, a rewritable magnetic tape, or some combination of the above. The media used by persistent storage 308 also may be removable. For example, a removable hard drive may be used for persistent storage 308.

Communications unit 310, in these examples, provides for communications with other data processing systems or devices. In these examples, communications unit 310 is a network interface card. Communications unit 310 may provide communications through the use of either or both physical and wireless communications links.

Input/output unit 312 allows for input and output of data with other devices that may be connected to data processing system 300. For example, input/output unit 312 may provide a connection for user input through a keyboard, a mouse, and/or some other suitable input device. Further, input/output unit 312 may send output to a printer. Display 314 provides a mechanism to display information to a user.

Instructions for the operating system, applications, and/or programs may be located in storage devices 316, which are in communication with processor unit 304 through communications fabric 302. In these illustrative examples, the instructions are in a functional form on persistent storage 308. These instructions may be loaded into memory 306 for execution by processor unit 304. The processes of the different embodiments may be performed by processor unit 304 using computer implemented instructions, which may be located in a memory, such as memory 306.

These instructions are referred to as program code, computer usable program code, or computer readable program code that may be read and executed by a processor in processor unit 304. The program code in the different embodiments may be embodied on different physical or computer readable storage media, such as memory 306 or persistent storage 308.

Program code 318 is located in a functional form on computer readable media 320 that is selectively removable and may be loaded onto or transferred to data processing system 300 for execution by processor unit 304. Program code 318 and computer readable media 320 form computer program product 322 in these examples. In one example, computer readable media 320 may be computer readable storage media 324 or computer readable signal media 326. Computer readable storage media 324 may include, for example, an optical or magnetic disk that is inserted or placed into a drive or other device that is part of persistent storage 308 for transfer onto a storage device, such as a hard drive, that is part of persistent storage 308. Computer readable storage media 324 also may take the form of a persistent storage, such as a hard drive, a thumb drive, or a flash memory, that is connected to data processing system 300. In some instances, computer readable storage media 324 may not be removable from data processing system 300. In these illustrative examples, computer readable storage media 324 is a non-transitory computer readable storage medium.

Alternatively, program code 318 may be transferred to data processing system 300 using computer readable signal media 326. Computer readable signal media 326 may be, for example, a propagated data signal containing program code 318. For example, computer readable signal media 326 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 318 may be downloaded over a network to persistent storage 308 from another device or data processing system through computer readable signal media 326 for use within data processing system 300. For instance, program code stored in a computer readable storage media in a server data processing system may be downloaded over a network from the server to data processing system 300. The data processing system providing program code 318 may be a server computer, a client computer, or some other device capable of storing and transmitting program code 318.

The different components illustrated for data processing system 300 are not meant to provide architectural limitations to the manner in which different embodiments may be implemented. The different advantageous embodiments may be implemented in a data processing system including components in addition to or in place of those illustrated for data processing system 300. Other components shown in FIG. 3 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 304 may take the form of a hardware unit that has circuits that are manufactured or configured for a particular use. This type of hardware may perform operations without needing program code to be loaded into a memory from a storage device to be configured to perform the operations.

For example, when processor unit 304 takes the form of a hardware unit, processor unit 304 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, programmable array logic, a field programmable logic array, a field programmable gate array, and other suitable hardware devices. With this type of implementation, program code 318 may be omitted because the processes for the different embodiments are implemented in a hardware unit.

In still another illustrative example, processor unit 304 may be implemented using a combination of processors found in computers and hardware units. Processor unit 304 may have a number of hardware units and a number of processors that are configured to run program code 318. With this depicted example, some of the processes may be implemented in the number of hardware units, while other processes may be implemented in the number of processors.

As another example, a storage device in data processing system 300 is any hardware apparatus that may store data. Memory 306, persistent storage 308, and computer readable media 320 are examples of storage devices in a tangible form.

In another example, a bus system may be used to implement communications fabric 302 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 306, or a cache, such as found in an interface and memory controller hub that may be present in communications fabric 302.

Figure 4:
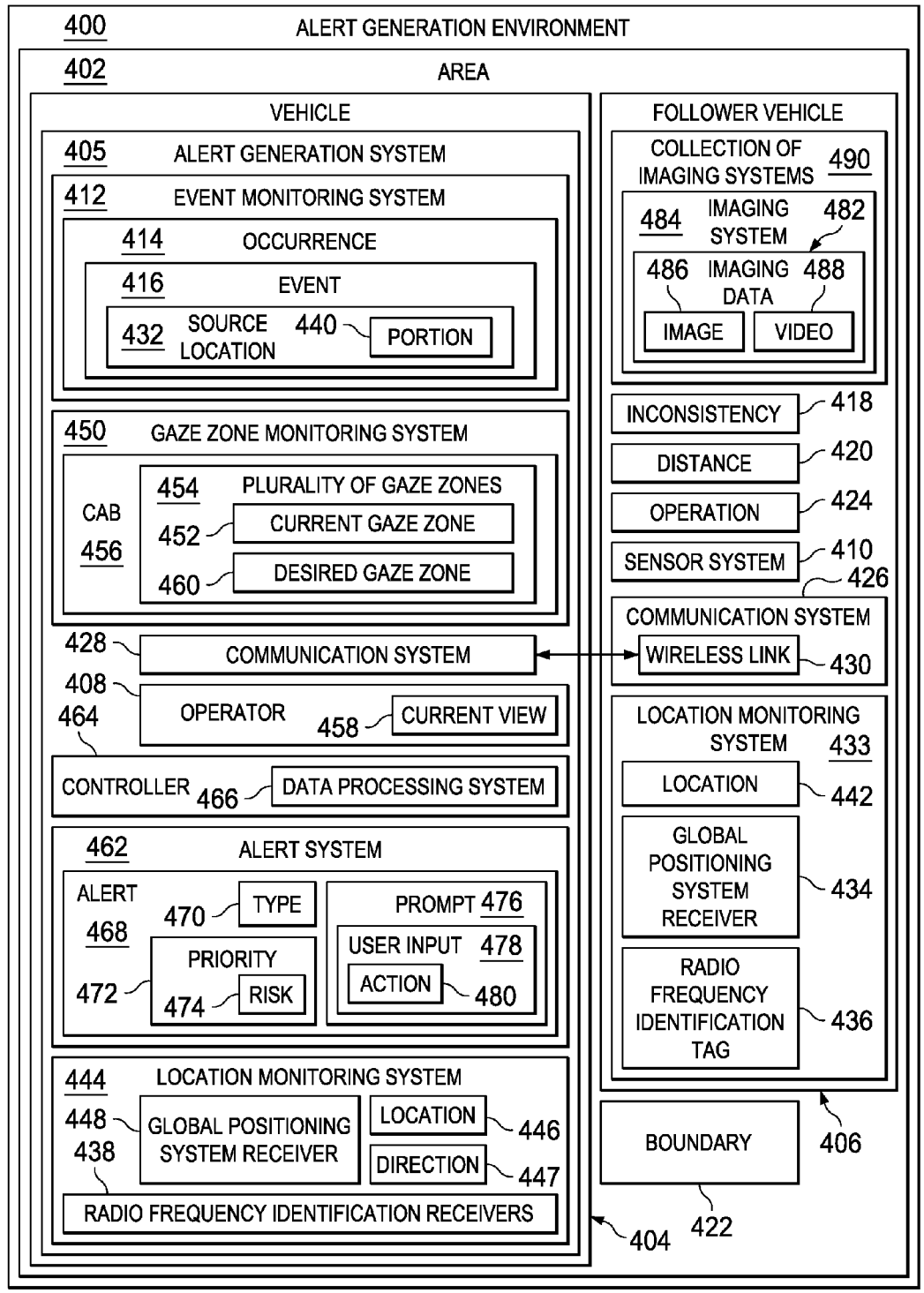
FIG. 4 is an illustration of a block diagram for an alert generation environment depicted in accordance with an illustrative embodiment.

Looking now to FIG. 4, an illustration of a block diagram for an alert generation environment is depicted in accordance with an illustrative embodiment. Alert generation environment 100 in FIG. 1 is an example of alert generation environment 400.

Alert generation environment 400 contains area 402. Area 402 is an area in which vehicle 404 and follower vehicle 406 operate. Vehicle 404 is an example implementation of vehicle 106 in FIG. 1. Follower vehicle 406 is an example of vehicle 110 in FIG. 1. Area 402 is an agricultural field in these examples. Of course, area 402 may be another area such as a parking lot, a lawn, or another suitable area.

Vehicle 404 performs an operation in area 402. The operation may be, for example, plowing area 402. Vehicle 404 is a leader vehicle for follower vehicle 406 in these examples. Vehicle 404 travels on a path through area 402, while follower vehicle 406 travels along the same or similar path. Of course, in other illustrative embodiments, follower vehicle 406 does not follow vehicle 404 and operates autonomously. In such illustrative embodiments, follower vehicle may use sensor systems, such as sensor systems 200 in FIG. 2, for route generation.

Operator 408 operates vehicle 404. Operating vehicle 404 means performing an operation using vehicle 404. The operation may include movement of vehicle 404. Vehicle 404 may use a propulsion system, such as an engine, to perform such movement. An example of an operation performed by vehicle 404 may be plowing area 402.

Follower vehicle 406 also operates in area 402. Follower vehicle 406 may be the same type of vehicle as vehicle 404 or another type of vehicle. For example, vehicle 404 may be a tractor and vehicle 406 may be a combine. Follower vehicle 406 uses sensor system 410 to identify the path traveled by vehicle 404. Sensor system 410 is an example of sensor system 200 in FIG. 2. Follower vehicle 406 then travels along the path traveled by vehicle 404 or along a similar path. A similar path is a path offset from the path traveled by vehicle 404 by an amount of time, a distance, or another suitable criteria.

As operator 408 operates vehicle 404 in area 402, alert generation system 405 operates systems onboard vehicle 404 in accordance with illustrative embodiments. In these examples, alert generation system 405 runs event monitoring system 412, gaze zone monitoring system 450, location monitoring system 444 and alert system 462. Event monitoring system 412 waits for occurrence 414 of event 416. Occurrence 414 of event 416 may be inconsistency 418 developing in follower vehicle 406 or an object associated with follower vehicle 406. For example, follower vehicle 406 may be a tractor. In such an illustrative embodiment, occurrence 414 of event 416 may be inconsistency 418 developing for the tractor or a plow being pulled by the tractor.

Of course, occurrence 414 of event 416 may be another type of event. For example, occurrence 414 of event 416 may also be follower vehicle 406 being located within distance 420 of boundary 422 for area 402. Boundary 422 may be a natural or man-made border for area 402. For example, boundary 422 may be a fence, a river bank, or another suitable border.

In some illustrative embodiments, occurrence 414 of event 416 is the completion of operation 424. Operation 424 is the operation being performed by follower vehicle 406. For example, follower vehicle 406 may be performing a mowing operation, a plowing operation, a harvesting operation, or another suitable operation. In such illustrative embodiments, occurrence 414 of event 416 is the completion of the operation for area 402 or a portion of area 402.

When event 416 occurs at follower vehicle 406, follower vehicle 406 uses communication system 426 to send data to communication system 428 onboard vehicle 404. Communication system 426 may use wireless link 430 to send the data. In these examples, the data consists of event 416, source location 432 for event 416, and the location of follower vehicle 406.

Follower vehicle 406 may identify the location of follower vehicle 406 using location monitoring system 433. In some illustrative embodiments, location monitoring system 433 is a component or contains components of sensor system 410. Location monitoring system 433 may identify location 442 of follower vehicle 406 on a local or global scale, for example, using global positioning system receiver 434. Global positioning system receiver 434 identifies latitude and longitude coordinates for the location of follower vehicle 406 using signals received from global positioning satellites.

Of course, in other illustrative embodiments, location monitoring system 433 identifies coordinates for the location of follower vehicle 406 local to area 402. For example, location monitoring system 433 may use a camera system to identify landmarks in area 402 with known coordinates to identify location 442 of vehicle 406. In yet other illustrative embodiments, location monitoring system 433 consists of radio frequency identification tag 436. Radio frequency identification tag 436 transmits an identity of follower vehicle 406 to the environment surrounding follower vehicle 406. In such illustrative embodiments, follower vehicle 406 transmits the identity of follower vehicle 406 to the environment surrounding follower vehicle 406 and does not send the location of follower vehicle 406 using wireless link 430. Of course, another suitable method for identifying and sending the location of follower vehicle 406 to vehicle 404 may be used.

Source location 432 is a system or portion 440 of follower vehicle 406 that caused occurrence 414 of event 416. For example, in some illustrative embodiments, occurrence 414 of event 416 is an object. The object causes a plow associated with follower vehicle 406 to become unable to continue plowing. In such an illustrative embodiment, source location 432 is portion 440 of follower vehicle 406. Portion 440 is the plow associated with follower vehicle 406 in this illustrative example. A tool or device, such as a plow, may be associated with follower vehicle 406 by being permanently or removably attached to follower vehicle 406. In some illustrative embodiments, the tool or device is pulled or pushed by the movement of follower vehicle 406.

Vehicle 404 receives location 442 of vehicle 406 using communication system 428. In some illustrative embodiments, vehicle 404 receives location 442 in the form of local or global coordinates. In such illustrative embodiments, vehicle 404 identifies direction 447 using location monitoring system 444 onboard vehicle 404. Direction 447 is the direction of follower vehicle 406 relative to vehicle 404. Location monitoring system 444 may identify the direction 447 relative to vehicle 404 by identifying location 446 of vehicle 404 using global positioning system receiver 448 or another suitable sensor. Location monitoring system 444 may then identify a vector between location 446 and location 442 to identify the direction 447 relative to vehicle 404.

In some illustrative embodiments, however, vehicle 404 receives location 442 of follower vehicle 406 in the form of a directional signal. For example, vehicle 404 may receive location 442 by receiving an identity from radio frequency identification tag 436 using radio frequency identification receivers 438 directionally. In other words, location monitoring system 444 may contain radio frequency identification receivers 438. In such an illustrative embodiment, location monitoring system 444 may identify that the transmission from radio frequency tag 436 is strongest in a particular direction. The particular direction is the direction 447 relative to vehicle 404.

Once the direction 447 relative to vehicle 404 is identified, gaze monitoring system 450 identifies current gaze zone 452 in plurality of gaze zones 454. In these examples, gaze monitoring system is located at least partially in cab 456 of vehicle 404. Cab 456 is an example of cab 114 in FIG. 1. Gaze monitoring system 450 divides cab 456 into plurality of gaze zones 454. Plurality of gaze zones 454 are portions of cab 456 that operator 408 in which or through which operator 408 may be looking.

Current gaze zone 452 is a gaze zone in plurality of gaze zones 454 that represents current view 458 of operator 408. Current view 458 is the direction in cab 456 in which operator 408 is presently looking. Gaze monitoring system 450 may identify current gaze zone 452 using eye tracking, head tracking, or another suitable tracking method.

Gaze zone monitoring system 450 also identifies desired gaze zone 460 using direction 447. Desired gaze zone 460 is the gaze zone in plurality of gaze zones 454 that includes direction 447. In some illustrative embodiments, desired gaze zone 460 is identified by controller 464, instead of gaze zone monitoring system 450. Controller 464 is data processing system 466 in these examples. Data processing system 300 in FIG. 3 is an example of data processing system 466.

Controller 464 then determines whether current gaze zone 452 is within desired gaze zone 460. In other words, controller 464 determines whether current view 458 is in direction 447. It should be noted that in some illustrative embodiments, plurality of gaze zones 454 do not include a height. In other words, current gaze zone 452 is the same when operator 408 changes current view 458 from the floor of cab 456 to the roof of cab 456 without changing the horizontal direction of the eyes or head. In other illustrative embodiments, plurality of gaze zones 454 may divide cab 456 into portions that include a height such that one gaze zone may include a vertical area up to a particular height, where another gaze zone begins.

In the event that current gaze zone 452 is within desired gaze zone 460, alert system 462 does not generate alert 468. In some illustrative embodiments, alert system 462 generates alert 468 within desired gaze zone 460 of cab 456. In other words, alert system 462 generates alert 468 using at least some components located in desired gaze zone 460 of cab 456. For example, alert 468 may be a visual alert using lights located within desired gaze zone 460 of cab 456. On the other hand, in the event that current gaze zone 452 is outside desired gaze zone 460, alert system 462 generates alert 468.

Alert 468 has type 470 and priority 472. Type 470 is the form of alert 468. For example, alert 468 may be an audio alert, such as an audible tone. Priority 472 is the importance of alert 468. Priority 472 of alert 468 is based on event 416. Alert system 462 may have a predetermined priority 472 for each event 416 that may occur with respect to vehicle 404 and/or follower vehicle 406.

Priority 472 may increase as risk 474 associated with event 416 increases, and priority 472 may decrease as risk 474 associated with event 416 decreases. For example, in an illustrative embodiment in which occurrence 414 of event 416 is follower vehicle 406 being located within distance 420 of boundary 422, risk 474 may increase as follower vehicle 406 moves closer to boundary 422 and distance 420 decreases. Priority 472 of alert 468 may set type 470 in some illustrative embodiments.

In some illustrative embodiments, alert 468 is interactive. In other words, alert 468 may include prompt 476. Prompt 476 requests user input 478 from operator 408. Prompt 476 requests that operator 408 perform action 480. For example, action 480 may consist of stopping operation of follower vehicle 406. Additionally, alert 468 may contain multimedia. For example, alert 468 may present imaging data 482. Imaging data 482 is generated by imaging system 484 associated with follower vehicle 406. Imaging data 482 may be in the form of image 486 and/or video 488.

Imaging system 484 may be in collection of imaging systems 490. Collection of imaging systems 490 is all imaging systems associated with follower vehicle 406. In these examples, follower vehicle 406 sends imaging data 482 from imaging system 484 for source location 432 in collection of imaging systems 490.

For example, in an illustrative embodiment in which occurrence 414 of event 416 is an obstruction causing the blade on a mower associated with follower vehicle 406 to stop operation, follower vehicle 406 sends imaging data 482 for imaging system 484 that generates data for source location 432. Source location 432 is the mower blade in this illustrative example.

The illustration of alert generation environment 400 in FIG. 4 is not meant to imply physical or architectural limitations to the manner in which different advantageous embodiments may be implemented. Other components in addition and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, in some illustrative embodiments, alert generation system 405 is data processing system 466. In such an illustrative embodiment, event monitoring system 412, gaze zone monitoring system 450, alert system 462, controller 464, and/or location monitoring system 444 are processes running on alert generation system 405.

Additionally, in some illustrative embodiments, follower vehicle 406 is an autonomous vehicle and does not follow vehicle 404. In such an illustrative embodiment, follower vehicle 406 may generate a route that allows follower vehicle 406 to complete a particular operation on area 402. For example, follower vehicle 406 may generate a route to mow area 402 without human intervention.

Figure 5:
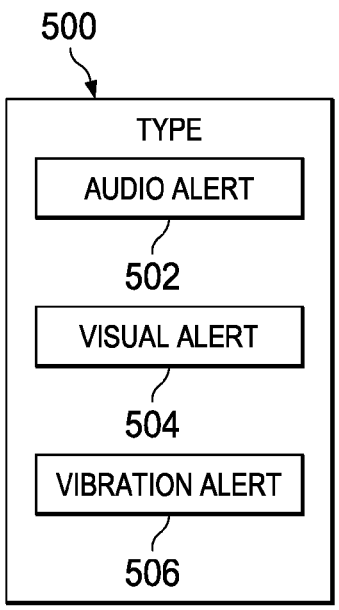
FIG. 5 is an illustration of a type of alert depicted in accordance with an illustrative embodiment.

Turning now to FIG. 5, an illustration of a type of alert is depicted in accordance with an illustrative embodiment. Type 500 is an example implementation of type 470 of alert 468 in FIG. 4.

Type 500 may be audio alert 502, in which the alert is an audible tone. Of course, the audio alert may also be music or a voice clip. The voice clip may be prerecorded or generated using text-to-speech conversion. In other illustrative embodiments, type 500 is visual alert 504. Visual alert 504 may be a written message, imaging data, a graphic, a light, or another suitable visual cue. Visual alert 504 may also include a request for user input. The user input may be a button, a switch, a voice command, or another suitable input.

Additionally, type 500 may be a vibration alert 506. For example, vibration alert 506 may cause an operator's seat, watch, cell phone, steering wheel, or other suitable device to vibrate. The speed, intensity, and frequency of vibration alert 506 may be based on the priority of the alert, such as priority 472 in FIG. 4. Of course, type 500 may consist of more than one type of alert, and one or more cues within each type of alert.

Figure 6:
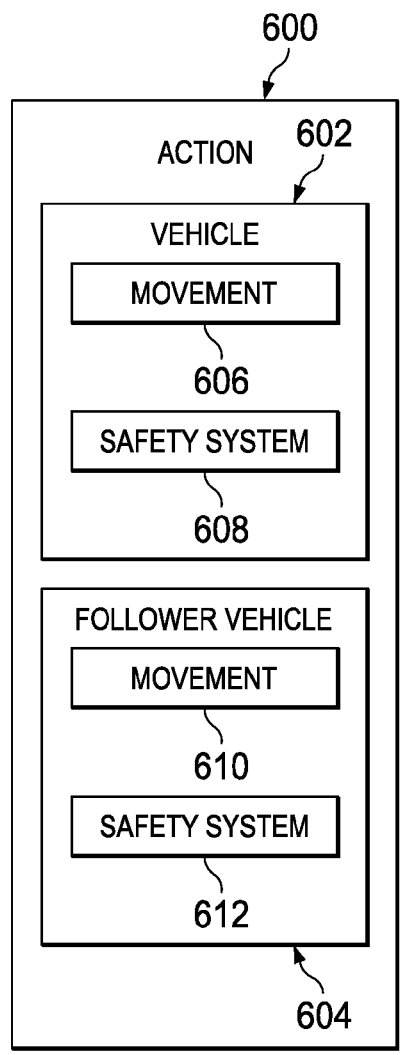
FIG. 6 is an illustration of an action depicted in accordance with an illustrative embodiment.

Looking now to FIG. 6, an illustration of an action is depicted in accordance with an illustrative embodiment. Action 600 is an example implementation of action 480 in FIG. 4.

Action 600 is an action that may be selected by a user in response to a prompt for user action, such as prompt 476 in FIG. 4. In these examples, action 600 is for vehicle 602, follower vehicle 604, or both. Vehicle 602 is an example of vehicle 404 in FIG. 4. Follower vehicle 604 is an example of follower vehicle 406 in FIG. 4. In some illustrative examples, action 600 is to stop movement 606 of vehicle 602. Likewise, action 600 may be to stop movement of 610 of follower vehicle 604. For example, an operator may desire to stop movement 610 to remove an object from a plow associated with follower vehicle 604 that has caused the plow to cease operation.

In other illustrative embodiments, action 600 consists of activating safety system 608 on vehicle 602, safety system 612 on follower vehicle 604, or both. Safety system 608 and safety system 612 are devices to inhibit an inconsistency in vehicle 602 or follower vehicle 604 from increasing in degree. For example, safety system 608 may be a robotic arm that clears objects from a plow that have caused the plow to function improperly.

Figure 7:
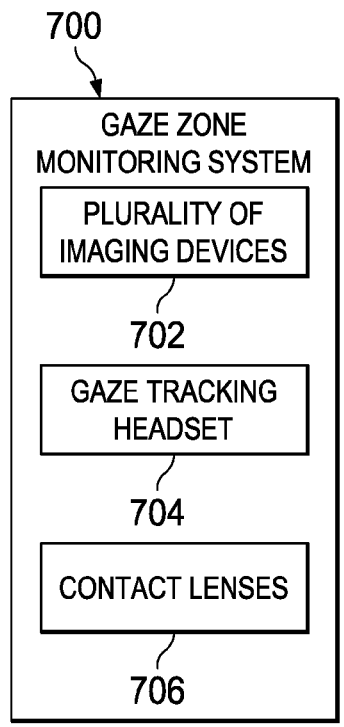
FIG. 7 is an illustration of a gaze zone monitoring system depicted in accordance with an illustrative embodiment.

Turning now to FIG. 7, an illustration of a gaze zone monitoring system is depicted in accordance with an illustrative embodiment. Gaze zone monitoring system 700 is an example implementation of gaze zone monitoring system 450 in FIG. 4.

Gaze zone monitoring system 700 may use one or more methods to identify a current gaze zone of an operator, such as current gaze zone 452 in FIG. 4. In some illustrative embodiments, gaze zone monitoring system 700 uses plurality of imaging devices 702 to identify the current gaze zone. Plurality of imaging devices 702 may generate imaging data, such as photo or video data. The imaging data may be visual light, infrared or another suitable light form.

In other illustrative embodiments, gaze zone monitoring system 700 is gaze tracking headset 704. Gaze tracking headset 704 uses motion tracking devices, such as accelerometers and/or gyroscopes, to identify a current gaze zone. In yet other illustrative embodiments, gaze zone monitoring system 700 uses contact lenses 706 worn by the operator and visible to sensors in the cab to identify the current gaze zone.

Figure 8:
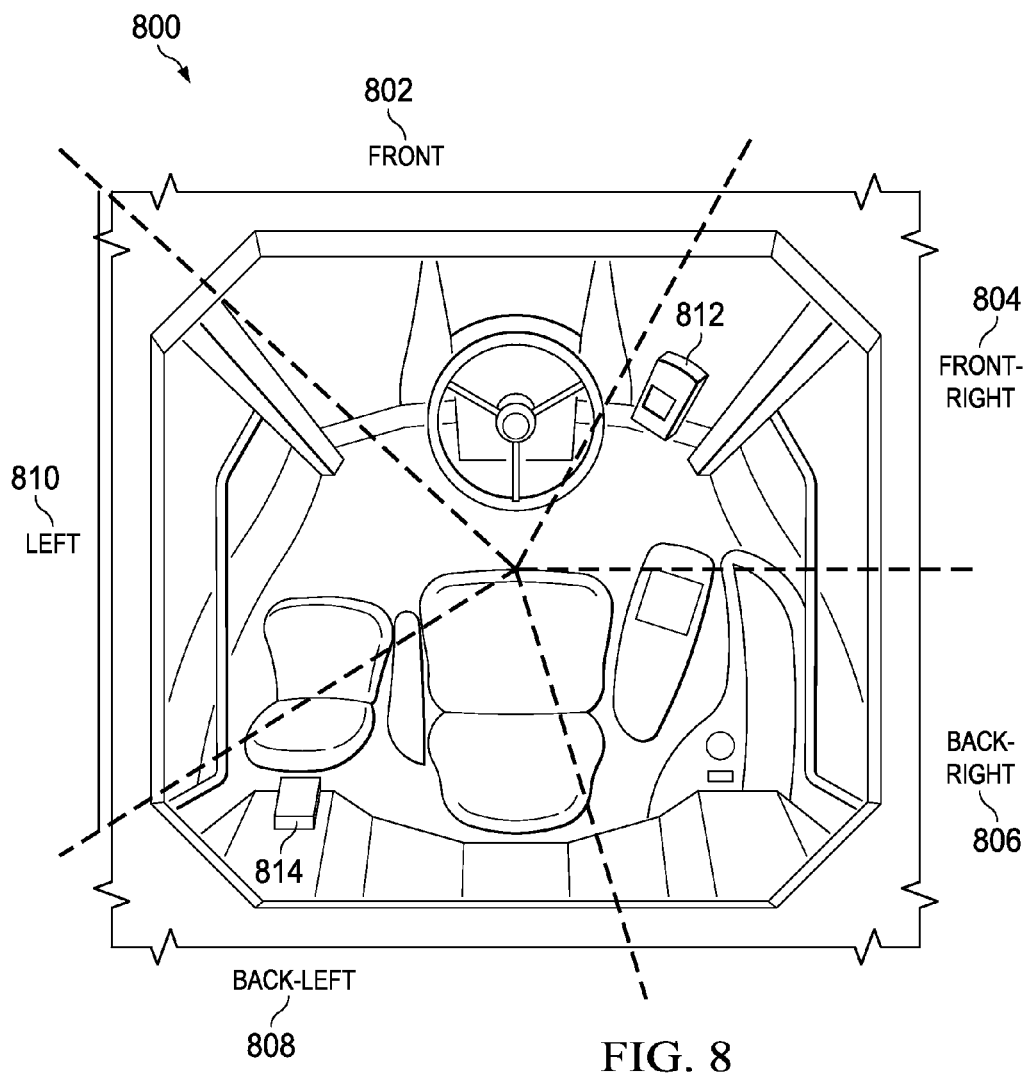
FIG. 8 is an illustration of a cab depicted in accordance with an illustrative embodiment.

Turning now to FIG. 8, an illustration of a cab is depicted in accordance with an illustrative embodiment. Cab 800 is an example implementation of cab 456 in FIG. 4.

Cab 800 is divided into gaze zones 802, 804, 806, 808, and 810. Cab 800 is depicted in a top view. Cab 800 may be divided into gaze zones by a gaze monitoring system, such as gaze zone monitoring system 450 in FIG. 4. In this illustrative example, cab 800 is divided into five gaze zones. The five gaze zones are asymmetrically sized in this example. In such an example, more gaze zones may be located where an operator is likely to be looking. However, in other illustrative embodiments, cab 800 is divided into symmetrically sized gaze zones.

Indicator 812 is a light and speaker unit that is a component of an alert system, such as alert system 462 in FIG. 4. In some illustrative embodiments, when an alert is generated in gaze zone 804, indicator 800 is used to generate the alert. For example, a sound may be played from indicator 800 and a light may be illuminated. However, when an alert is generated in gaze zone 808, indicator 814 is used to generate the alert. An indicator may be present in some of gaze zones 802, 804, 806, 808, and 810, all of gaze zones 802, 804, 806, 808, and 810, or no gaze zones in the different illustrative embodiments.

Figure 9:
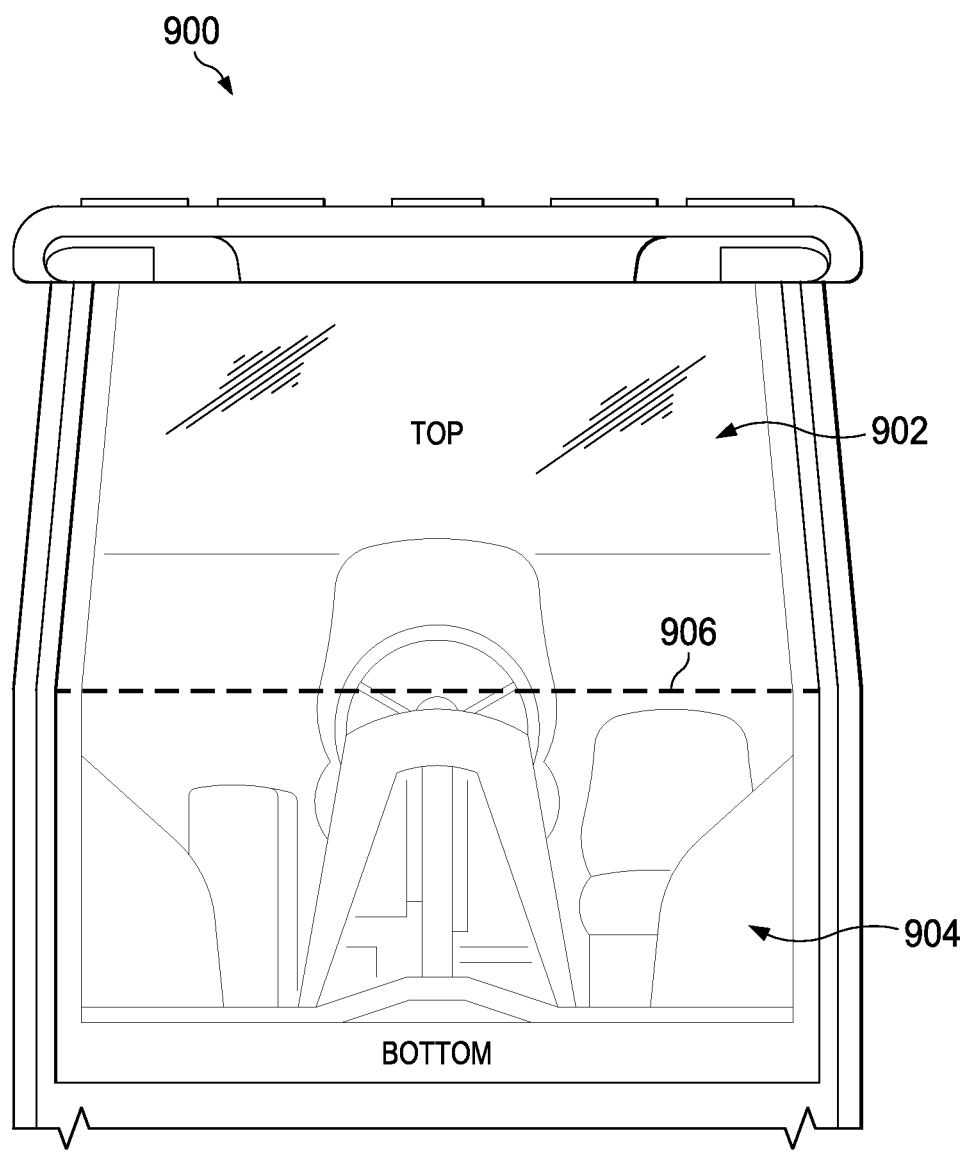
FIG. 9 is another illustration of a cab depicted in accordance with an illustrative embodiment.

Looking now to FIG. 9, another illustration of a cab is depicted in accordance with an illustrative embodiment. Cab 900 is an example implementation of cab 456 in FIG. 4. Cab 900 is divided into gaze zones 902 and 904. Cab 900 is depicted in a side view in this example. Gaze zone 902 begins at the floor of cab 900 and extends to divider 906. Divider 906 is a virtual partition between gaze zone 902 and gaze zone 904.

While gaze zones 902 and 904 are depicted in this example, gaze zones 902 and 904 divide each of gaze zones 802, 804, 806, 808, and 810 in FIG. 8 in other examples. Thus, for example, gaze zone 802 may be divided into two gaze zones: one gaze zone beginning at the floor and extending toward the roof of cab 900 until a divider, such as divider 906, is encountered. A second gaze zone divided from gaze zone 802 may begin at the roof of cab 900 and extend to divider 906.

Figure 10:
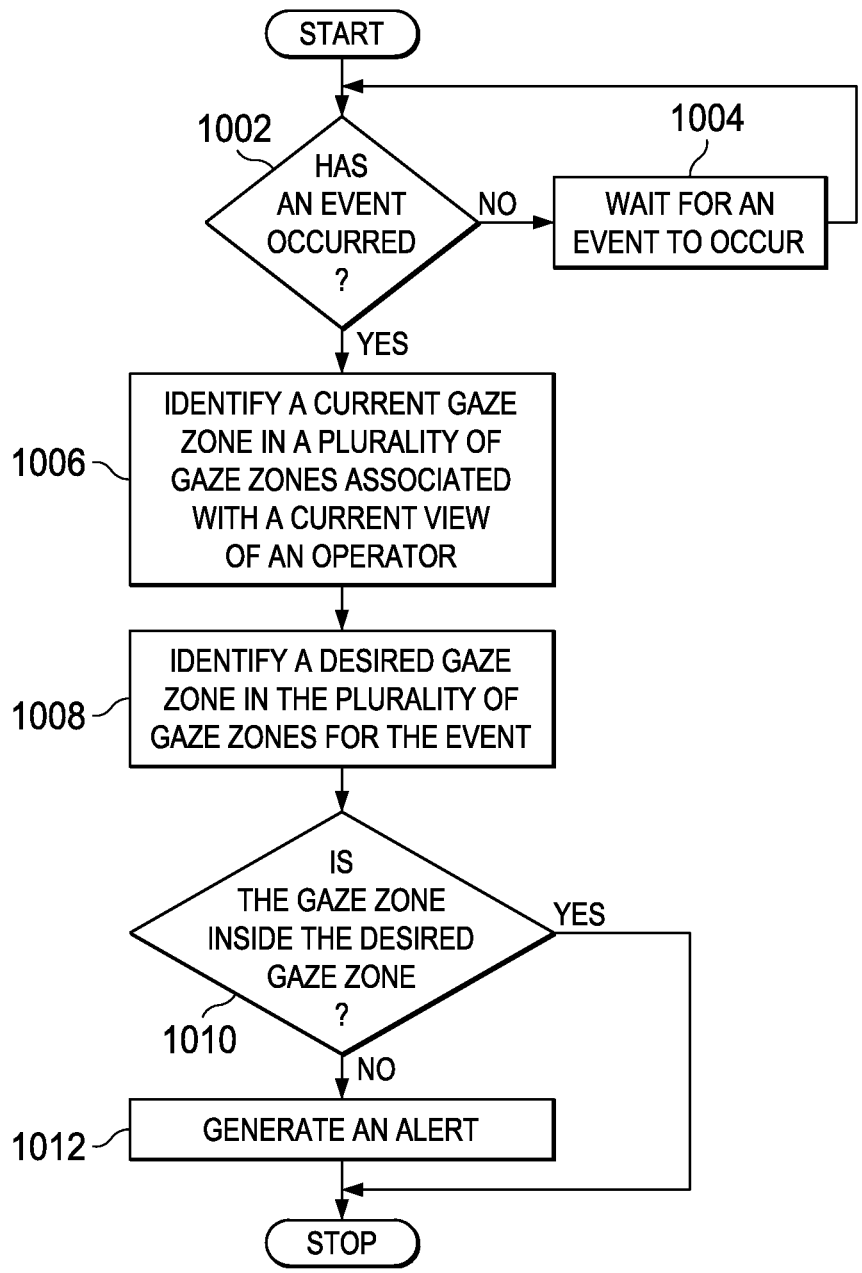
FIG. 10 is a flowchart of process for generating alerts depicted in accordance with an illustrative embodiment.

Turning now to FIG. 10, a flowchart of a process for generating alerts is depicted in accordance with an illustrative embodiment. The process may be performed by alert generation system 405 in vehicle 404 in FIG. 4.

The process begins by determining whether an event has occurred (step 1002). The event may be an event such as event 416 in FIG. 4. For example, the event may be that a follower vehicle is approaching a boundary of the area in which the follower vehicle is operating and is located within a particular distance of the boundary.

If at step 1002 the process determines that an event has not occurred, the process waits for an event to occur (step 1004) and returns to step 1002. If at step 1002 the process determines that an event has occurred, the process identifies a current gaze zone in a plurality of gaze zones associated with a current view of the operator (step 1006). The plurality of gaze zones may be located in the cab of a vehicle being operated by an operator. A gaze monitoring system may divide the cab into a plurality of gaze zones and identify the gaze zone of the operator. The current gaze zone is the gaze zone in the plurality of gaze zones that contains the current view of the operator.

The process identifies a desired gaze zone in the plurality of gaze zones for the event (step 1008). The process determines whether the gaze zone is inside the desired gaze zone (step 1010). If at step 1010 the process determines that the gaze zone is inside the desired gaze zone, the process terminates. However, if at step 1010 the process determines that the gaze is not inside the desired gaze zone, the process generates an alert (step 1012). The alert may be an alert such as alert 468 in FIG. 4. The alert may have a type, such as video or audio, and a priority. As the risk of the event increases, the priority may also increase. As priority increases, the alert may be longer, louder, brighter, or another suitable condition. The process terminates thereafter.

Figure 11:
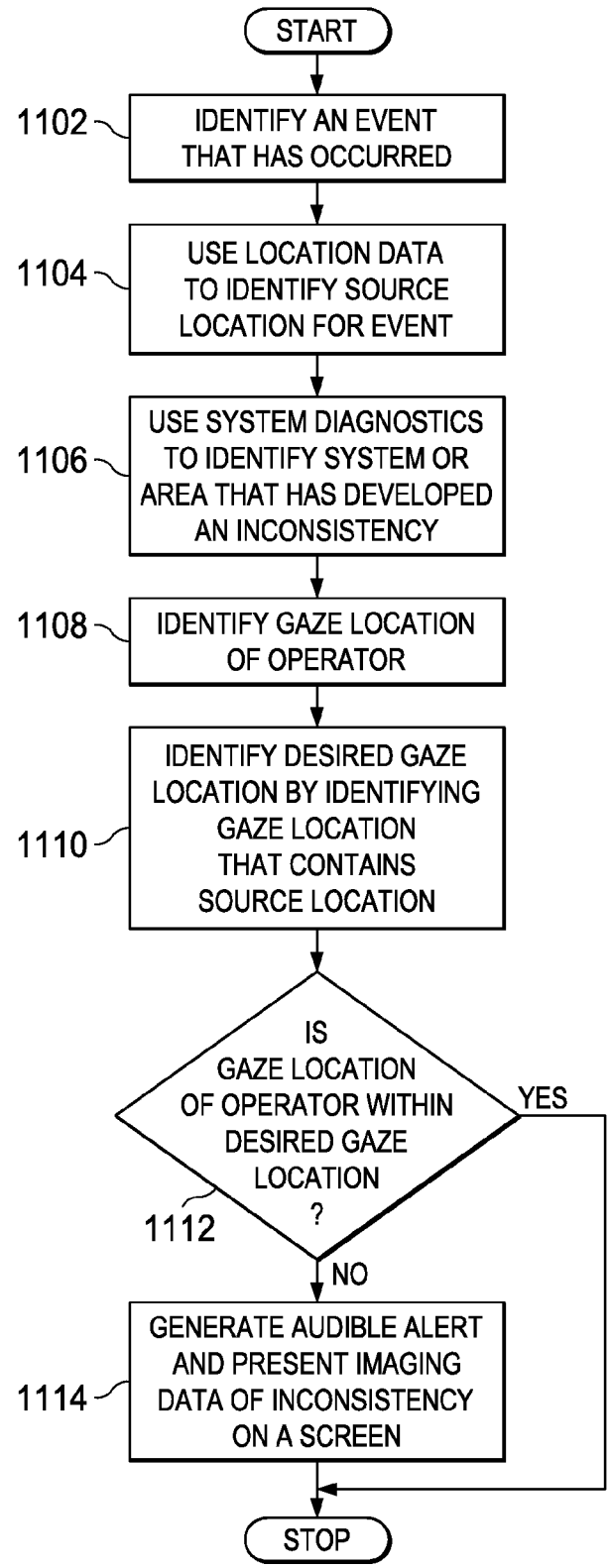
FIG. 11 is another flowchart of a process for generating alerts depicted in accordance with an illustrative embodiment.

Looking now to FIG. 11, another flowchart of a process for generating alerts is depicted in accordance with an illustrative embodiment. The process may be performed by alert generation system 405 in vehicle 404 in FIG. 4.

The process begins by identifying an event that has occurred (step 1102). The event may be an event such as event 416 in FIG. 4. For example, the event may be that a follower vehicle is approaching a boundary of the area in which the follower vehicle is operating and is located within a particular distance of the boundary. Of course, the event may be an event for the vehicle in which the alert generation system is located in some illustrative embodiments. For example, an inconsistency may develop in a plow being pulled by the vehicle.

The process uses location data to identify a source location for an event (step 1104). The location data may be generated by a location monitoring system such as location monitoring system 444 in FIG. 4. The location data may consist of global positioning data, local positioning data, or position data for a follower vehicle relative to the vehicle.

The process then uses system diagnostics to identify the system or area that has developed an inconsistency (step 1106). The system diagnostics consist of determining whether the systems on a vehicle are operating within normal parameters. Next, the process identifies the gaze location of the operator (step 1108). The process then identifies the desired gaze location by identifying a gaze location that contains a source location (step 1110). The source location is a source location such as source location 432 in FIG. 4. The source location is a location where the event occurred. For example, when the event is an object causing a plow to stop operating, the plow is the source location.

The process determines whether the gaze location of the operator is within the desired gaze location (step 1112). If at step 1112 the process determines that the gaze location of the operator is within the desired gaze location, the process terminates. However, if at step 1112 the process determines that the gaze location of the operator is not within the desired gaze location, the process generates an audible alert and presents imaging data of the inconsistency on a screen (step 1114). The process terminates thereafter.

The flowcharts and block diagrams in the different depicted embodiments illustrate the architecture, functionality, and operation of some possible implementations of apparatus, methods and computer program products. In this regard, each block in the flowchart or block diagrams may represent a module, segment, or portion of computer usable or readable program code, which comprises one or more executable instructions for implementing the specified function or functions. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

For example, the process may generate an alert at operation 1010 when the current gaze zone of the operator is in a gaze zone adjacent to the desired gaze zone. The alert may have a lower priority than an alert generated for a current gaze zone on the opposite side of the cab from the desired gaze zone. The alert with lower priority may only illuminate a light or present a visual, inaudible message in a graphical user interface.

Thus, the different illustrative embodiments allow an operator to increase the safety of the operation of machinery and vehicles by receiving alerts when the operator is not focused on an object or area which is to be focused on for proper operation of the machinery or vehicle. The different illustrative embodiments also allow an operator to receive alerts only when the operator is not already focused on the object or area. Reducing the number of the alerts is advantageous because alerts that are generated may be given additional attention by an operator who does not frequently receive alerts.

Thus, the different illustrative embodiments provide a method, apparatus, and computer program product for generating alerts. Responsive to an occurrence of an event, a current gaze zone in a plurality of gaze zones associated with a current view of an operator is identified. A desired gaze zone in the plurality of gaze zones is identified for the event. The desired gaze zone contains a source location for the event. A determination is made whether the current gaze zone is inside the desired gaze zone. Responsive to a determination that the current gaze zone is outside the desired gaze zone, an alert is generated.

The description of the different illustrative embodiments has been presented for purposes of illustration and description, and is not intended to be exhaustive or limited to the embodiments in the form disclosed. Many modifications and variations will be apparent to those of ordinary skill in the art. Further, different embodiments may provide different advantages as compared to other embodiments. The embodiment or embodiments selected are chosen and described in order to best explain the principles of the invention, the practical application, and to enable others of ordinary skill in the art to understand the invention for various embodiments with various modifications as are suited to the particular use contemplated.

What is claimed is:

1. A method for generating alerts comprising:
responsive to an occurrence of an event, identifying a current gaze zone in a plurality of gaze zones associated with a current view of an operator;

identifying a desired gaze zone in the plurality of gaze zones for the event, wherein the desired gaze zone contains a source location for the event;

determining whether the current gaze zone is inside the desired gaze zone; and responsive to a determination that the current gaze zone is outside the desired gaze zone, generating an alert, wherein the alert comprises a prompt for user input to perform an action, and wherein the action is selected from stopping a first movement of a vehicle in which the operator is located, stopping a second movement of a follower vehicle following the vehicle, activating a first safety system on the vehicle, and activating a second safety system on the follower vehicle.

2. The method of claim 1, wherein the step of generating the alert comprises generating the alert within the desired gaze zone.

3. The method of claim 1 further comprising:
prior to generating the alert, identifying a priority for the alert based on the event.

4. The method of claim 2, wherein the priority for the alert increases with a risk of the event, and the priority for the alert decreases with the risk of the event.

5. The method of claim 2, wherein the alert is selected from a group comprising an audio alert, a visual alert, and a vibration alert.

6. The method of claim 1 further comprising:
prior to generating the alert, identifying a type for the alert based on the event, wherein the type for the alert is imaging data of the source location.

7. The method of claim 6, wherein the operator is located in a vehicle, and the imaging data of the source location is generated by an imaging system located on a follower vehicle of the vehicle.

8. The method of claim 7, wherein the occurrence of the event comprises an inconsistency developing in the follower vehicle.

9. The method of claim 7, wherein the occurrence of the event comprises the follower vehicle being located within a distance of a boundary for an area in which the follower vehicle is operating.

10. A method for generating alerts comprising:
responsive to an occurrence of an event, identifying a current gaze zone in a plurality of gaze zones associated with a current view of an operator;
identifying a desired gaze zone in the plurality of gaze zones for the event, wherein the desired gaze zone contains a source location for the event;
determining whether the current gaze zone is inside the desired gaze zone;
responsive to a determination that the current gaze zone is outside the desired gaze zone, generating an alert;
prior to generating the alert, identifying a type for the alert based on the event, wherein the type for the alert is imaging data of the source location, wherein the operator is located in a vehicle, and the imaging data of the source location is generated by an imaging system located on a follower vehicle of the vehicle, and wherein the occurrence of the event comprises the follower vehicle completing an operation being performed by the follower vehicle.

11. A method for generating alerts comprising:
responsive to an occurrence of an event, identifying a current gaze zone in a plurality of gaze zones associated with a current view of an operator;
identifying a desired gaze zone in the plurality of gaze zones for the event, wherein the desired gaze zone contains a source location for the event;
determining whether the current gaze zone is inside the desired gaze zone;
responsive to a determination that the current gaze zone is outside the desired gaze zone, generating an alert, wherein the step of generating the alert comprises presenting imaging data of the source location; and
prior to presenting the imaging data of the source location, identifying an imaging system from a collection of imaging systems that generates the imaging data for the source location.

12. The method of claim 11, wherein the imaging data is selected from an image and a video, and wherein the source location is a portion of the follower vehicle.

13. An apparatus comprising:
an event monitoring system configured to identify an occurrence of an event and identify a desired gaze zone in the plurality of gaze zones for the event, wherein the desired gaze zone contains a source location for the event;
a gaze zone monitoring system configured to identify a current gaze zone in a plurality of gaze zones associated with a current view of an operator responsive to an occurrence of an event;
a controller configured to determine whether the current gaze zone is within the desired gaze zone; and
an alert system configured to generate an alert responsive to a determination that the current gaze zone is outside the desired gaze zone, wherein the alert system is further configured to generate the alert within the desired gaze zone.

14. The apparatus of claim 13 further comprising:
a location monitoring system configured to identify the source location for the event.

15. The apparatus of claim 14, wherein the location monitoring system is associated with a follower vehicle of a vehicle operated by the operator.

16. The apparatus of claim 15, wherein the source location is the location of the follower vehicle.

17. The apparatus of claim 13, wherein the alert system is further configured to identify a priority for the event.

18. The apparatus of claim 13, wherein the priority for the alert increases with a risk of the event, and the priority for the alert decreases with the risk of the event.

19. The apparatus of claim 13, wherein the alert is selected from a group comprising an audio alert, a visual alert, and a vibration alert.

20. The apparatus of claim 13, wherein the alert system is further configured to identify a type for the alert based on the event, and wherein the type for the alert is imaging data of the source location.

21. The apparatus of claim 13, wherein the operator is located in a vehicle, and further comprising:
an imaging system located on a follower vehicle of the vehicle configured to generate the imaging data of the source location.

22. The apparatus of claim 21, wherein the occurrence of the event comprises an inconsistency developing in the follower vehicle.

23. An apparatus comprising:
an event monitoring system configured to identify an occurrence of an event and identify a desired gaze zone in the plurality of gaze zones for the event, wherein the desired gaze zone contains a source location for the event;

a gaze zone monitoring system configured to identify a current gaze zone in a plurality of gaze zones associated with a current view of an operator responsive to an occurrence of an event;
a controller configured to determine whether the current gaze zone is within the desired gaze zone;
an alert system configured to generate an alert responsive to a determination that the current gaze zone is outside the desired gaze zone; and
a location monitoring system configured to identify the source location for the event, wherein the location monitoring system is associated with a follower vehicle of a vehicle operated by the operator and the source location is the location of the follower vehicle;
wherein the location monitoring system comprises a first global positioning system receiver associated with the vehicle and a second global positioning system receiver associated with the follower vehicle.

24. An apparatus comprising:
an event monitoring system configured to identify an occurrence of an event and identify a desired gaze zone in the plurality of gaze zones for the event, wherein the desired gaze zone contains a source location for the event;
a gaze zone monitoring system configured to identify a current gaze zone in a plurality of gaze zones associated with a current view of an operator responsive to an occurrence of an event;
a controller configured to determine whether the current gaze zone is within the desired gaze zone;
an alert system configured to generate an alert responsive to a determination that the current gaze zone is outside the desired gaze zone; and
a location monitoring system configured to identify the source location for the event, wherein the location monitoring system is associated with a follower vehicle of a vehicle operated by the operator and the source location is the location of the follower vehicle;
wherein the location monitoring system comprises a radio frequency identification receiver associated with the vehicle and a radio frequency identification tag associated with the follower vehicle.

25. A computer program product comprising:
computer readable program code, stored on a computer readable storage medium, for identifying a current gaze zone in a plurality of gaze zones associated with a current view of an operator responsive to an occurrence of an event;
computer readable program code, stored on the computer readable storage medium, for identifying a desired gaze zone in the plurality of gaze zones for the event, wherein the desired gaze zone contains a source location for the event;
computer readable program code, stored on the computer readable storage medium, for determining whether the current gaze zone is inside the desired gaze zone; and
computer readable program code, stored on the computer readable storage medium, for generating an alert responsive to a determination that the current gaze zone is outside the desired gaze zone, wherein the alert comprises a prompt for user input to perform an action, and wherein the action is selected from stopping a first movement of a vehicle in which the operator is located, stopping a second movement of a follower vehicle following the vehicle, activating a first safety system on the vehicle, and activating a second safety system on the follower vehicle.

* * * * *